(12) United States Patent
Reed

(10) Patent No.: US 7,426,865 B2
(45) Date of Patent: Sep. 23, 2008

(54) METHOD FOR ULTRASONIC ELASTIC MODULUS CALCULATION AND IMAGING

(75) Inventor: Francis Alexander Reed, Duanesburg, NY (US)

(73) Assignee: General Electric Company, Schenectady, NY (US)

( * ) Notice: Subject to any disclaimer, the term of this patent is extended or adjusted under 35 U.S.C. 154(b) by 420 days.

(21) Appl. No.: 11/284,656

(22) Filed: Nov. 22, 2005

(65) Prior Publication Data

US 2007/0113655 A1    May 24, 2007

(51) Int. Cl.
  *G01N 29/07* (2006.01)
(52) U.S. Cl. ........................................ 73/597
(58) Field of Classification Search ............... 73/597; 600/443
  See application file for complete search history.

(56) References Cited

U.S. PATENT DOCUMENTS

| | | | | |
|---|---|---|---|---|
| 3,746,121 A | * | 7/1973 | Niklas | 73/597 |
| 4,432,234 A | * | 2/1984 | Jones | 73/597 |
| 5,178,147 A | * | 1/1993 | Ophir et al. | 600/437 |
| 5,339,691 A | * | 8/1994 | Smith et al. | 73/597 |
| 5,700,955 A | * | 12/1997 | Roth | 73/597 |
| 6,478,741 B2 | | 11/2002 | Chiao et al. | 600/447 |
| 6,534,964 B1 | * | 3/2003 | Sinha | 73/597 |
| 6,856,175 B2 | | 2/2005 | Wodnicki | 327/108 |
| 2003/0033878 A1 | | 2/2003 | Dubois et al. | 73/600 |

* cited by examiner

*Primary Examiner*—John E Chapman
(74) *Attorney, Agent, or Firm*—Cantor Colburn LLP

(57) ABSTRACT

Disclosed herein is a method and apparatus for generating an image of an article, wherein the image represents the articles elastic modulus. The method comprises the steps of measuring a time of flight value at a point on a test sample utilizing ultrasonic sound waves, measuring the position of the point, calculating a thickness value for the test sample, calculating a velocity value utilizing the time of flight value and the thickness value, calculating a density value for the test sample, calculating a Poisson's ratio value for the test sample, calculating an elastic modulus value utilizing the velocity value, the density value, and the Poisson's ratio value, assigning a shade of gray, or a color, to the elastic modulus values on the image, and, constructing an image utilizing the position of the point and the shaded, or colored, elastic modulus values.

15 Claims, 3 Drawing Sheets
(1 of 3 Drawing Sheet(s) Filed in Color)

2.0 *10⁶ psi                    2.5*10⁶ psi 2.0 *10⁶ psi                                       2.5*10⁶ psi

METHOD FOR ULTRASONIC ELASTIC MODULUS CALCULATION AND IMAGING

TECHNICAL FIELD

This disclosure generally relates to an apparatus and method for nondestructive elastic modulus measurement and image construction thereof.

BACKGROUND

Determination of the mechanical properties of manufactured articles is useful for predicting the performance and applications of new articles and compositions as well as ensuring consistent quality of existing processes and/or articles of manufacture. One such property that can be evaluated is the modulus of elasticity (e.g., Young' modulus, elastic modulus). The modulus of elasticity is a measure of a material's relative stiffness, or more specifically, a measure of the rate of change in stress with respect to strain.

One method of determining the modulus of elasticity (E) for a composition or article is through tensile testing. Tensile testing first comprises securing a sample of known dimensions between an upper moving jaw and a bottom stationary jaw, which are disposed at a known distance therebetween. Once secured, the upper jaw can advance in a direction away from the bottom jaw, which generates a tensile force on the test article. The resulting stress is plotted with respect to the strain generated, wherein the modulus of elasticity is equal to the slope of the graph. This principle is illustrated in equation (I) below;

$$E = \frac{\text{stress}}{\text{strain}} = \frac{\left(\frac{F}{A}\right)}{\left(\frac{d}{l}\right)}$$

Wherein;

$E$ = Modulus of Elasticity
$F$ = Measured Force
$A$ = Area
$d$ = Extension Length
$l$ = Original Length Although tensile testing can be utilized to calculate the modulus of elasticity for an article, the test is destructive, which can present manufacturers with a loss in profit. Furthermore, tensile testing cannot predict changes in the modulus of elasticity across an article; rather, tensile testing is a measurement of the article's gross properties.

As a result, manufacturers desire a method for testing the mechanical properties of articles without the need for destructive mechanical testing, and further desire a test method that comprises the fidelity to determine the modulus of elasticity across an entire surface of the article.

BRIEF SUMMARY

Disclosed herein are apparatus and methods for non-destructively determining the modulus of elasticity of an article.

In one embodiment, an ultrasonic measurement apparatus comprises: a scanning apparatus comprising an ultrasonic transducer and a X-Y head and a computer. The ultrasonic transducer is capable of measuring the time of flight of ultrasonic sound waves, while the computer is connected in operable communication with the ultrasonic transducer and the X-Y head. The connection with the ultrasonic transducer can supply the computer with time of flight data, and the connection with the X-Y head can supply the computer with position data. The computer is capable of utilizing the time of flight data and position data to calculate an elastic modulus value. The relative motion can be created between the ultrasonic transducer and a sample.

In one embodiment, the method for calculating an elastic modulus value comprises: measuring a time of flight for a point on a sample utilizing ultrasonic sound waves, wherein the sample has a thickness, a Poisson's ratio, and a density, calculating a velocity of the ultrasonic sound wave utilizing the time of flight and the thickness, and determine an elastic modulus for the point utilizing the velocity, the density, and the Poisson's ratio.

In another embodiment, the method for generating an image of an article comprises: measuring a time of flight at a point on a sample utilizing ultrasonic sound waves, wherein the sample has a Poisson's ratio and a density, determining a position of the point, determining a point thickness for the test sample at the point, calculating a velocity utilizing the time of flight and the point thickness, determining a point elastic modulus utilizing the velocity, the density, and the Poisson's ratio, assigning a color to the point elastic modulus, and creating an elastic modulus image utilizing the position of the point and the color.

The above described and other features are exemplified by the following figures and detailed description.

BRIEF DESCRIPTION OF THE DRAWINGS

"The patent or application file contains at least one drawing executed in color. Copies of this patent or patent application publication with color drawings will be provided by the Office upon receipt and payment of the necessary fee."

Refer now to the figures, which are exemplary embodiments, and wherein the like elements are numbered alike.

DETAILED DESCRIPTION

Figure 1:
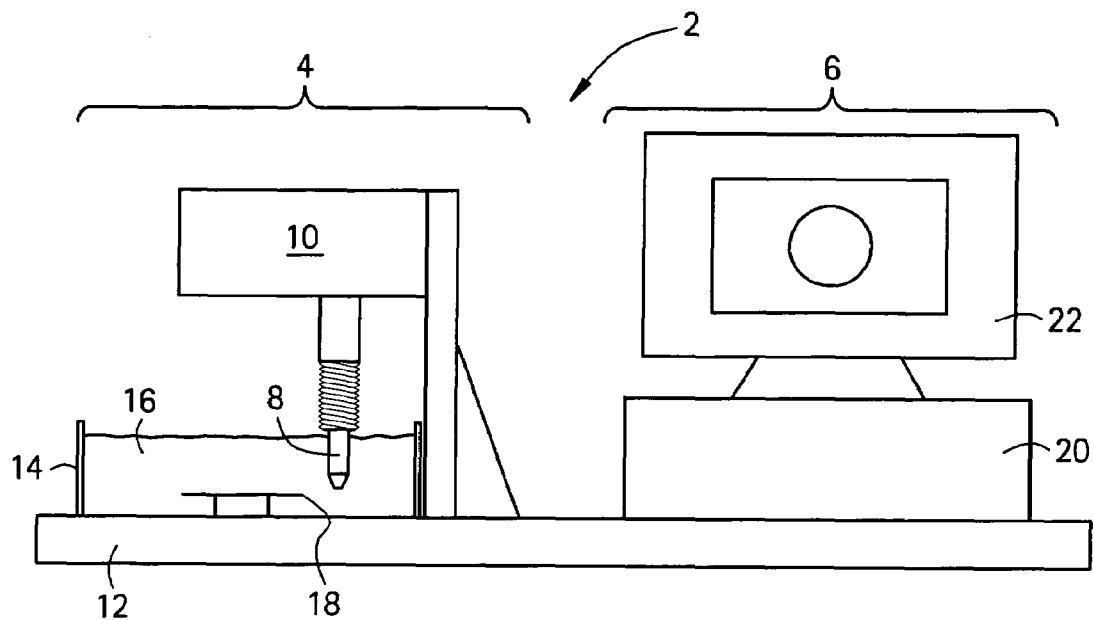
FIG. 1 is a side view of an exemplary ultrasonic measuring apparatus.

Ranges herein are inclusive and independently combinable (e.g., ranges of "up to about 25 wt %, with about 5 wt % to about 20 wt % desired", is inclusive of the endpoints and all intermediate values of the ranges of "about 5 wt % to about 25 wt %," etc). The terms "first," "second," and the like, herein do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). Also, the terms "front", "back", "bottom", and/or "top" are used herein, unless otherwise noted, merely for convenience of description, and are not limited to any one position or spatial orientation. The suffix "(s)" as used herein is intended to include both the singular and the plural of the term that it modifies, thereby including one or more of that term (e.g., the metal(s) includes one or more metals).

Disclosed herein is a method for satisfying the unmet needs of manufacturers by employing ultrasonic measurement methods to generate data that can be combined with material property data to calculate the modulus of elasticity of an article for multiple points on the articles surface. Thereafter, the modulus of elasticity data can be utilized to generate an image of the article's modulus of elasticity for visual analysis.

Ultrasonic sound waves (greater than 20 kilohertz) can be employed for ultrasonic imaging, depth measurement, and flow rate measurement. In thickness measurement applications for example, the time required for a sound wave to travel through an articles mass, reflect off the other side of the article, and travel back to the point of origin can be utilized to calculate the thickness of the article. This time can also be referred to as the "time of flight" of the signal. The thickness calculation employs time (t) and velocity (V) to calculate the thickness (T), as illustrated in equation I;

$$T = \left(\frac{Vt}{2}\right) \quad \text{(I)}$$

T = Thickness
V = Velocity
t = time

To measure the time (t), an ultrasonic transducer can be employed, which is capable of emitting an ultrasonic wave(s) and sensing the reflected signal. Ultrasonic transducers can be employed in direct contact and indirect contact systems. In direct contact systems, the ultrasonic transducer is disposed in direct contact with one surface of the test specimen and the sound waves are emitted directly onto the surface of the article. Direct contact systems can be employed in many applications, such as wall thickness measurement of pipes. Direct contact transducers can also employ a delay line, which is utilized in applications designed to measure articles that comprise a thin wall thickness. The delay line transducer comprises a delay element that can be positioned between the transducer element and the article, which increases the delay between the initial signal and the reflected signal. a delay element can comprise materials such as a polymers, ceramics, metals, and the like, as well as combinations comprising at least one of the following. In non-direct contact systems, an ultrasonic transducer is disposed a distance away from the test specimen and in contact with a conductive media in which the article is disposed. The conductive media is capable of transmitting the emitted sound wave(s) from the ultrasonic transducer to the part, and the reflected signal back to the article. It is to be noted that air exhibits poor ultrasonic wave transmission.

Once the ultrasonic transmitter determines the time of flight of the sound wave, the velocity of the signal is utilized to determine the thickness. The velocity (V) value is generated through calibration of the ultrasonic measurement apparatus. The purpose of calibrating the velocity is because the velocity at which the ultrasonic signal travels within an article varies with respect to a plurality of variables (e.g., density, stiffness, temperature). Therefore, calibration can increase the accuracy of the velocity measurements and thus the thickness calculation.

An apparatus can be constructed to generate a plurality of ultrasonic thickness measurements that can be employed to construct a visual image of an article. This can be beneficial to allow for visual inspection of manufactured articles. An image of an article's thickness can be constructed by translating an ultrasonic transducer (e.g., or scan multiple transducers) across the surface of an article. As the transducer translates (e.g., scans) the surface of the article, a plurality of ultrasonic time of flight measurements can be taken at points across the surface of the article. The ultrasonic data gathered, and the respective position of each point, can then be utilized to calculate thickness measurements for each point a measurement was taken. The various thicknesses can then be assigned a shade of gray or a color that can be utilized to assemble an image of the article (e.g., grayscale image, Raster color image). For example, in an exemplary thickness measurement application, the thickness of an integrated circuit board can be determined across the circuit boards top surface. In this embodiment, the ultrasonic measurements can be measured in rows comprising points that are 0.10 millimeters from the next point. The ultrasonic measurements can be saved with data corresponding to the position of the ultrasonic measurement. Next, the ultrasonic measurements can be utilized to calculate a thickness for each point. After the thicknesses have been calculated for each point, an image can be created. The image is created by first assigning a shade of gray, or a color, (e.g., light shades or colors can correspond to thin thicknesses and dark shades or dark colors can correspond to thicker wall thicknesses) to the thickness values for each point. Next, the shaded or colored points can be assembled into an image, wherein each shaded or colored point corresponds to a pixel. The resulting image can then be utilized for inspection purposes, such as to evaluate if abnormalities in thickness are present, if the position of a defect is acceptable or is not acceptable, evaluating trends in abnormal thicknesses, and for information necessary to troubleshoot and/or perfect a process.

As with imaging thickness of an article, it is envisioned that it is desirable for manufacturers and/or researchers to have the capability to create visual images of an article's modulus of elasticity. This capability allows manufacturers and/or researchers the ability to evaluate the presence of abnormalities in an article's modulus of elasticity, analyze the position of defects, evaluate trends, troubleshoot, and so forth. Visual imaging will also reduce destructive testing, and hence reduce waste. For example, tensile testing can be employed to calculate the modulus of elasticity of manufactured articles. However, the cost of destructively testing many manufactured goods can reduce manufacturing profits. Therefore, an ultrasonic transducer can be utilized to scan the surface of an article to generate time of flight data that can be employed in conjunction with other material property data to calculate the modulus of elasticity at multiple points across the surface of an article. This data enables the construction of a visual image of the article's modulus across the surface of the article.

The modulus of elasticity (e.g., Young's modulus) can be calculated per equation II:

$$E = V^2 \rho \left[\frac{(1+\mu)(1-2\mu)}{(1-\mu)}\right] \quad \text{(II)}$$

Wherein;

E = Modulus of Elasticity
V = Velocity
ρ = Density
μ = Poisson's Ratio

In the equation, values for the velocity of sound travel (V), density (ρ), and the Poisson's ratio (μ) are used to calculate the modulus of elasticity (E). For an article comprising uniform thickness (T), the density of the article can be determined by a multitude of methods, such as that shown in equation III:

$$\rho = \frac{m}{V} \quad \text{(III)}$$

Wherein;

ρ = density
m = mass
V = volume

Next, the Poisson's ratio can be calculated by conducting mechanical testing, such as tensile testing, on samples of the article. Poisson's ratio (μ) can be calculated by equation IV.

$$\mu = \frac{\left(\frac{\Delta l}{l}\right)}{\left(\frac{\Delta w}{w}\right)} \quad \text{(IV)}$$

Wherein;

μ = Poisson's Ratio
Δl = Change in Length
l = length
Δw = Change in Width
w = Width In addition, Poisson's ratio (μ) can be determined by conducting mechanical testing on a sample and graphing stress vs. strain, wherein the slope of the resulting curve is equal to the modulus of elasticity and using the modulus of elasticity value to solve equation II for the Poisson's ratio (μ).

Once the density and Poisson's ratio have been calculated, the article can be scanned by an ultrasonic transducer to generate time of flight (t) values for points across the surface of the article. Each time value can be employed to calculate a velocity (V) for each point by solving equation (I) for velocity (V), utilizing the known thickness of the article. As shown below in equation (V).

$$V = \frac{2T}{t} \quad \text{(V)}$$

Wherein;

V = velocity
T = thickness
t = time

Once the velocity, density, and Poisson's ratio are known, the modulus of elasticity can be calculated at each point measured. The modulus of elasticity data can then be assigned a shade or color, and a visual image (e.g., grayscale image, Raster image, and so forth) can be created as a visual representation of the elastic modulus of the article.

Similar to the process for calculating and imaging the elastic modulus for articles comprising a known thickness, this process can also be conducted to generate a modulus of elasticity image for articles that comprise a non-uniform thickness. In this method, the velocity of sound travel (V), density (ρ), and Poisson's ratio (μ) are again used to determine the modulus of elasticity (E) per equation II. More specifically, the density and Poisson's ratio are calculated utilizing similar methods to those disclosed above (e.g., density can be calculated utilizing equation III, and the Poisson's ratio can be calculated by conducting mechanical testing, such as tensile testing, utilizing per equation IV). However, to calculate the modulus of elasticity, the velocity of the ultrasonic wave is used. As illustrated in equation (V), to determine the velocity, the thickness and time of flight are used. Therefore, the thickness is determined prior to or at the same time as the time of flight is measured for each point.

The thickness can be determined utilizing any method, such as, but not limited to, optical measurement methods (e.g., comparator), magnetic force measurement systems (e.g., rolling ball), manual measurement methods (e.g., calipers, micrometers), eddy current methods, magnetic induction methods, and the like. For example, an apparatus can comprise an ultrasonic transducer and a non-ultrasonic thickness measurement system. The ultrasonic transducer can be capable of determining the time of flight of an ultrasonic wave through the article, and the thickness measurement system can comprise an upper and lower surface probes (e.g., caliper) to measure the thickness of the surface. Furthermore, the exemplary apparatus can be capable of creating relative motion between the system and the article (e.g., of translating the ultrasonic transducer and thickness measurement system across the surface of the article) and measuring the time of flight and thickness at a plurality of points across the surface of the article. The ultrasonic time of flight data and thickness data are then utilized to calculate the velocity of the ultrasonic waves, which can then be employed to calculate the modulus of elasticity for each point. The modulus of elasticity data can then be assigned a shade of gray that represents a thickness (e.g., lighter shades for relatively thin sections and darker shades for relatively thick sections) and each point measured can comprise a pixel, or group of pixels, in a visual image generated from the data.

The apparatus capable of calculating and generating an image based on modulus of elasticity data can be any apparatus, such as, but is not limited to, a processor(s), computer(s), and so forth, and can employ memory, storage, register(s), timing, interrupt(s), communication interfaces(s), input/output signal interface(s), and so forth, as well as combinations comprising at least one of the foregoing. Furthermore, the apparatus can include input signal processing and filtering capabilities that enable accurate sampling and conversion of acquisitions of such signals from various sensor(s), including pulser and/or receive signal conditioning boards. For example, ultrasonic transducer(s), thickness measurement systems, and the like can be employed that are capable of producing a signal that is capable of operating with the apparatus.

Various ultrasonic transducer(s) can be employed. For example, an array of ultrasonic transducer elements can be used to transmit an ultrasound beam and then receive the reflected beam from the article. Such scanning comprises a series of measurements in which the focused ultrasonic wave is transmitted, the system switches to receive mode after a short time interval, and the reflected ultrasonic wave is received. Transmission and reception can be focused in the same direction during each measurement to acquire data from a series of points along an acoustic beam or scan line, while the receiver can be dynamically focused at a succession of ranges along the scan line as the reflected ultrasonic waves are received.

Optionally, high-voltage components can be included in the transmit circuitry to drive the individual ultrasound transducer elements, while low-voltage, high-density digital logic circuitry can be used to provide transmit signals to the high-voltage drivers. The high-voltage drivers typically operate at voltages of up to approximately 100 volts, while the low-voltage logic circuitry has an operating voltage on the order of 5 volts in the case of TTL logic. The high-voltage drivers may be fabricated as discrete components or as integrated circuits, while the low-voltage logic circuitry may be fabricated as a separate integrated circuit or combined with the high-voltage circuitry on a single chip. In addition to transmit circuitry including the high-voltage drivers and low-voltage logic circuitry, the transducer head may include low-noise, low-voltage analog receive circuitry. The low-voltage receive circuitry, like the transmit logic circuitry, typically has an operating voltage on the order of 5 volts or so, and may be a separate integrated circuit or may be fabricated with the low-voltage transmit logic circuitry as a monolithic integrated circuit. Possible ultrasonic transducer(s) include those described in U.S. Pat. No. 6,856,175 to Wodnicki.

Refer now to FIG. 1, which is a side view of an exemplary ultrasonic measurement apparatus 2. The ultrasonic measurement apparatus 2 comprises a scanning apparatus 4 and a computer 6. The scanning apparatus 4 comprises an ultrasonic transducer 8 operably connected to a X-Y head 10. The X-Y head 10 is secured to a base 12. a tank 14 is disposed under the X-Y head 10 in which a sonically conductive fluid 16 is held. Supported within the sonically conductive fluid 16 is a test sample 18. a central processing unit 20 (hereinafter referred to as "CPU") is also disposed on the base 12, is connected in operable communication with the ultrasonic transducer 8 and with a monitor 22.

The ultrasonic transducer(s) 8 can comprise any design or configuration that is capable of emitting an ultrasonic signal and measuring the same. For example, the ultrasonic transducer 8 can comprise a linear array of transducers, comprising about ten or more transducers. The ultrasonic transducer 8 can be constructed to provide a prolonged service life submerged in sonically conductive fluid 16. In one embodiment, a protective casing can be disposed around the transducer, which is sealed at the tip for durability.

The X-Y head 10 can comprise any apparatus that can translate the ultrasonic transducer 8 over the top surface of the test sample 18, or that allows relative motion to be created between the X-Y head 10 and the test sample 18. In one embodiment, the X-Y head 10 can comprise servo controlled ball slide(s) with linear encoder(s) connected to, and controlled by, the CPU 20. The X-Y head 10 can be constructed for a prolonged service life and can be fixtured and/or supported to minimize vibration.

CPU 20 can comprise any processing unit capable of receiving and/or sending data, signals, electrical communications, and/or instructions to and from the scanning apparatus 4, receiving input from a user (e.g., keyboard, mouse, touch-screen), as well as employing said data, signals, electrical communication, and/or instructions to calculate mechanical property data (e.g., elastic modulus) and generate an image of said mechanical property data. For example, in one embodiment, the CPU 20 can receive and send communications to the ultrasonic transducer 8 and X-Y head 10 to measure the ultrasonic time of flight across the test sample 10 at points across the test sample 10 as instructed by user inputted variables (e.g., X-Y measurement points to be 0.2 millimeters apart). Further, the CPU 20 can utilize the data gathered from the ultrasonic measurements, and data inputted from a user (e.g., density, velocity) to calculate the elastic modulus of a test sample 10. Once calculated, the results of each calculation for each point measured can be assigned a shade of gray (i.e. grayscale imaging) or color (i.e., Raster or Pixel imaging) to construct an image of the elastic modulus that geometrically represents the test sample 10 on the monitor 22.

The computer 6 can also comprise software, hardware and/or programming that can enable a user to conduct further analysis of the image displayed on the monitor 22. Such analysis can comprise view modification capabilities (e.g., to view larger or smaller sections of the image), measuring capabilities (e.g., distance measurement, calculation of average mechanical properties within a selected portion of the image), and the like.

In one embodiment, the ultrasonic transducer 8 can be capable of emitting an ultrasonic sound wave that can be transmitted through the sonically conductive fluid 16 to the interface of the sonically conductive fluid 16 and the test sample 18, at which, at least a portion of the ultrasonic sound wave will reflect off of the interface and can be measured by the ultrasonic transducer 8. The time of flight of the ultrasonic wave can be calculated from the instant the wave was emitted, was reflected off of the interface, and then was received at the ultrasonic transducer 8. In addition, at least a portion of the ultrasonic sound wave will travel through the test sample 18, reflect off the bottom surface of the test sample, and travel back to the ultrasonic transducer 8 where it can be measured and its time of flight can be calculated.

Figure 2:
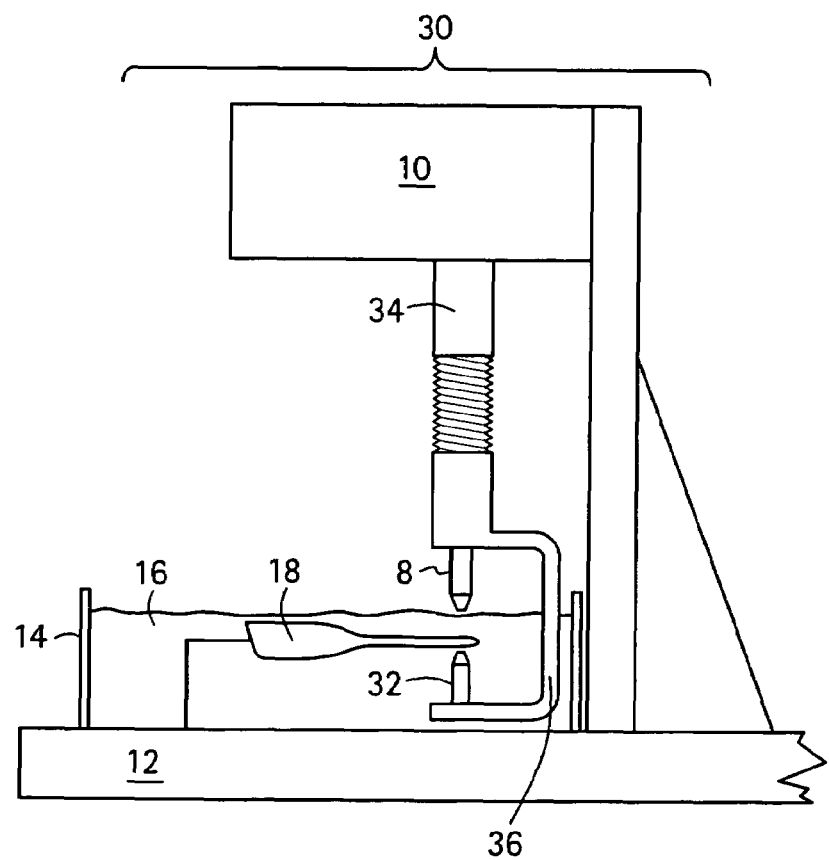
FIG. 2 is a side view of another exemplary ultrasonic measuring apparatus.

Referring now to FIG. 2, a modified scanning apparatus, generally designated 30, is illustrated. In the illustration, the modified scanning apparatus 30 can comprise an ultrasonic transducer 8 connected to an X-Y head 10 via an arm 34. Connected to the arm 34 can be a lower ultrasonic transducer 32, which is connected via a caliper 36. The arm 34 and caliper can be connected in operable communication to the computer (not shown), which can control the motion of the arm 34 and caliper 36, which are capable of extending and retracting to position the ultrasonic transducer 8 and lower ultrasonic transducer 32 (herein after referred to as "transducers") at a distance from the test sample 18. The modified scanning apparatus 30 functions similar to the scanning apparatus 2, however, the lower ultrasonic transducer 32 can enable the measurement of a test sample 18 comprising a non-uniform thickness.

In operation, the transducers can be controlled via the computer 6 (see FIG. 1) along the surface contours of the test sample 18 by utilizing an ultrasonic sound wave reflected off the interface of the sonically conductive fluid 16 and the test sample 18 to adjust the distance of the transducers from the top and bottom surfaces of the test sample 18. Within the caliper 36 can be a linear encoder (not shown) that can supply a distance at which the caliper 36 is extended. These distances can then be employed by the computer 6 to calculate the thickness of the test sample 18.

In another embodiment, the modified scanning apparatus can comprise a thickness measurement tool (not shown) in lieu of the lower ultrasonic transducer 32 that can be capable of measuring the thickness of the test sample 18. The thickness measurement tool can be capable of measuring thickness of the test sample 18 utilizing any method (e.g., optical measurement methods (e.g., comparator), magnetic force measurement systems (e.g., rolling ball), manual measurement methods (e.g., calipers, micrometers), eddy current methods, magnetic induction methods).

EXAMPLES

Figure 3:
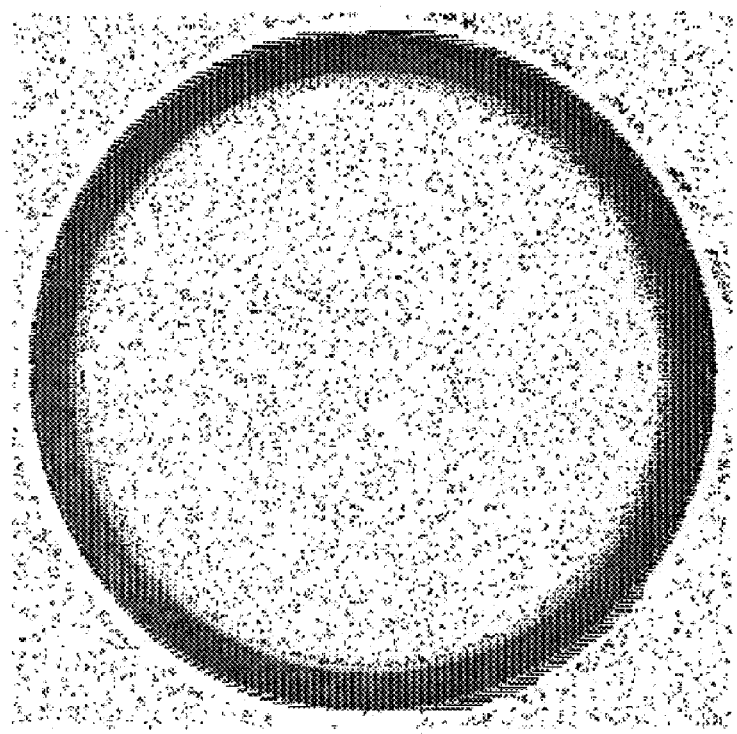
FIG. 3 is an exemplary grayscale image of the elastic modulus of a carbon-graphite composite ring.

Referring now to FIG. 3, an exemplary grayscale image of the elastic modulus of a carbon-graphite composite ring is illustrated. To construct the illustration, a carbon-graphite seal was analyzed utilizing a SONIX immersion-type ultrasonic scanner and a MATEC ultrasonic instrument. The carbon-graphite seal comprised a uniform thickness of about 1.32 centimeters (cm), an internal diameter of about 17.3 cm, and an external diameter of about 20.5 cm. The points were collected in a raster pattern with a separation of 0.063 cm (0.025 in) between adjacent points along the scan line and also perpendicular to the scan line. The seal was supported within an immersion tank and ultrasonically analyzed. The time of flight measurements were stored for each point analyzed. The time of flight data was then imported into MATHCAD 12 wherein each time of flight measurement, and its respective location (e.g., X-Y coordinates), was employed to calculate an elastic modulus in a geometrically similar image for each point measured, with inputted variables (e.g., thickness, density). The elastic modulus data points were then assigned a shade of gray based on the range of elastic modulus values calculated and a grayscale image was generated representing the elastic modulus of the ring in the geometrically similar representation of the ring.

Figure 4:
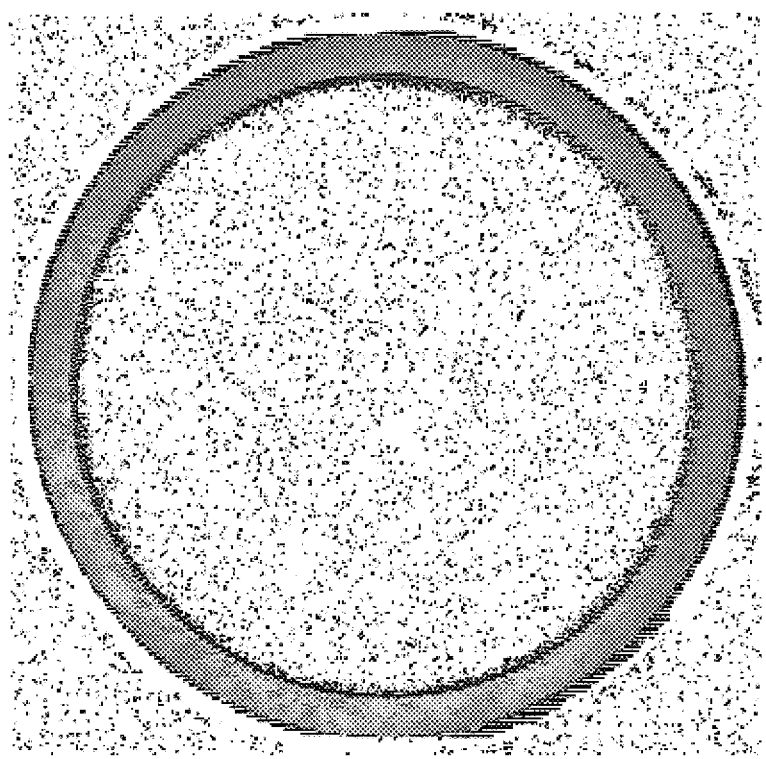
FIG. 4 is an exemplary Raster color image of the elastic modulus of a carbon-graphite composite ring.
Figure 4:

Referring now to FIG. 4, an exemplary Raster color image of the elastic modulus of a carbon-graphite composite ring. To construct the Raster color image, the elastic modulus data generated for the creation of FIG. 3 was assigned a color with respect to the range of elastic modulus values calculated, and a geometrically similar image was generated.

One of the primary benefits of utilizing ultrasonic measurement techniques is that the method is non-destructive. Therefore, the methods and apparatus disclosed herein can be employed to non-destructively determine an article's modulus of elasticity through calculation employing the ultrasonic measurements along with some inherent material property data, without destroying possibly otherwise saleable articles. This process enables manufacturers and researchers to reduce and/or eliminate loss of profits due to destructive testing. Another advantage of the methods and apparatus disclosed herein is that the images created can be utilized for inspection purposes, such as evaluating if abnormalities in the modulus of elasticity, location of modulus of elasticity defects, acceptability of defects, evaluation of trends in modulus of elasticity values, and/or evaluation of information that can enable troubleshooting of manufacturing processes. Such analytical information can assist manufacturers and researchers in the development of new and useful articles, increase process yields, and identify new applications for known articles. In conclusion, for these reasons, the method and apparatus disclosed herein can benefit the state of the art of analytical measurement techniques and offer manufacturers, researchers, and the like, a valuable analytical tool.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An ultrasonic measurement apparatus, comprising:
    a scanning apparatus comprising an ultrasonic transducer and a X-Y head, wherein the ultrasonic transducer is capable of measuring the time of flight of ultrasonic sound waves;
    a computer, wherein the computer is connected in operable communication with the ultrasonic transducer and the X-Y head, wherein the connection with the ultrasonic transducer can supply the computer with time of flight data, and the connection with the X-Y head can supply the computer with position data; and,
    wherein the computer is capable of utilizing the time of flight data, and position data to calculate an elastic modulus value, wherein the computer is capable of assigning a color to the elastic modulus and generating an image of the elastic modulus; and
    wherein relative motion can be created between the ultrasonic transducer and a sample.

2. The ultrasonic measurement apparatus of claim 1, wherein the color is a shade of gray to the elastic modulus value and generating an image of the shaded elastic modulus on the monitor.

3. The ultrasonic measurement apparatus of claim 1, wherein the image of the colored elastic modulus value is on a monitor.

4. The ultrasonic measurement apparatus of claim 1, further comprising a lower ultrasonic transducer.

5. The ultrasonic measurement apparatus of claim 1, further comprising a thickness measurement tool.

6. The ultrasonic measurement apparatus of claim 1, further comprising
    a user interface, which enables a user to input information into the computer; and
    a monitor, which is connected in operable communication to the computer, wherein the monitor can display information.

7. A method for calculating an elastic modulus value, comprising:
    measuring a time of flight for a point on a sample utilizing ultrasonic sound waves, wherein the sample has a thickness, a Poisson's ratio, and a density;
    calculating a velocity of the ultrasonic sound wave utilizing the time of flight and the thickness;
    determine an elastic modulus for the point utilizing the velocity, the density, and the Poisson's ratio;
    determining a range of the elastic modulus determined;
    assigning a color to each point based on the range of elastic modulus determined; and
    creating a color image representing the elastic modulus of each point of the sample.

8. The method of claim 7, wherein the sample has a variable thickness, further comprising determining a point thickness for the point.

9. The method of claim 8, wherein determining the point thickness further comprises measuring the point thickness with an ultrasonic transducer.

10. The method of claim 7, further comprising determining the density.

11. The method of claim 7, further comprising
    measuring a time of flight for each point on the sample utilizing ultrasonic sound waves;
    calculating a velocity of each of the ultrasonic sound waves; and,
    determine an elastic modulus for each point.

12. The method of claim 7, wherein the color is a shade of gray, and wherein the color image is a grayscale image.

13. A method for generating an image of an article, comprising:

measuring a time of flight at a point on a sample utilizing ultrasonic sound waves, wherein the sample has a Poisson's ratio and a density;

determining a position of the point;

determining a point thickness for the test sample at the point;

calculating a velocity utilizing the time of flight and the point thickness;

determining a point elastic modulus utilizing the velocity, the density, and the Poisson's ratio;

assigning a color to the point elastic modulus; and creating an elastic modulus image utilizing the position of the point and the color.

14. The method for of claim 13, wherein determining the point thickness further comprises measuring the thickness with an ultrasonic transducer.

15. The method of claim 13, wherein the color is a shade of gray.

* * * * *